(12) United States Patent
Zerick et al.

(10) Patent No.: US 11,064,945 B2
(45) Date of Patent: *Jul. 20, 2021

(54) DETERMINING FOOD IDENTITIES WITH INTRA-ORAL SPECTROMETER DEVICES

(71) Applicant: AT&T Intellectual Property I, L.P., Atlanta, GA (US)

(72) Inventors: Juliette Zerick, Alpharetta, GA (US); Eugene Rascle, Saint Helena Island, SC (US); William Cottrill, Canton, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/443,348

(22) Filed: Jun. 17, 2019

(65) Prior Publication Data
US 2019/0307398 A1 Oct. 10, 2019

Related U.S. Application Data

(63) Continuation of application No. 16/126,611, filed on Sep. 10, 2018, now Pat. No. 10,321,875, which is a
(Continued)

(51) Int. Cl.
*A61B 5/00* (2006.01)
*A61C 7/08* (2006.01)
(Continued)

(52) U.S. Cl.
CPC .......... *A61B 5/682* (2013.01); *A61B 5/0031* (2013.01); *A61B 5/0075* (2013.01);
(Continued)

(58) Field of Classification Search
CPC ..... A61B 5/682; A61B 5/0075; A61B 5/4866; A61B 5/486; A61B 5/7405; A61B 5/742;
(Continued)

(56) References Cited

U.S. PATENT DOCUMENTS 4,629,424 A * 12/1986 Lauks ................. A61B 5/0002
257/417
4,966,141 A * 10/1990 Bacaner ............... A61B 5/0205
128/207.14
(Continued)

FOREIGN PATENT DOCUMENTS

JP 2014163905 A * 9/2014
KR 2008-0094139 10/2008
(Continued)

OTHER PUBLICATIONS

Hintschich et al, MEMS-based miniature near-infrared spectrometer for application in environmental and food monitoring; proceedings of the 8th international Conference on Sensing Technology, pp. 432-433 (Year: 2014).*
(Continued)

*Primary Examiner* — Daryl C Pope (57) ABSTRACT

Devices, methods, computer-readable media, and systems for determining an identity of a food are disclosed. For example, a method may receive at least one property of at least one component in a sample of a food from an intra-oral device including a spectrometer, the at least one property obtained via the spectrometer, compares the at least one property to a plurality of food signatures, and determines the identity of the food based upon the comparing. In another example, a system may include an intra-oral device and a wireless device. The intra-oral device may include a spectrometer for measuring at least one property of at least one component in a sample of a food. The wireless device may include a processor for receiving the at least one property, comparing the at least one property to a plurality of food signatures, and determining the identity of the food based upon the comparing.

12 Claims, 5 Drawing Sheets

Related U.S. Application Data continuation of application No. 15/824,863, filed on Nov. 28, 2017, now Pat. No. 10,070,818, which is a continuation of application No. 15/092,142, filed on Apr. 6, 2016, now Pat. No. 10,058,283.

(51) Int. Cl.
*A61C 8/00* (2006.01)
*A61B 5/145* (2006.01)
*G09B 19/00* (2006.01)
*G01N 33/02* (2006.01)
*G01N 21/31* (2006.01)
*H01J 49/00* (2006.01)
*G01N 21/27* (2006.01)
*A61C 5/00* (2017.01)
*A61C 5/20* (2017.01)

(52) U.S. Cl.
CPC .......... *A61B 5/14539* (2013.01); *A61B 5/486* (2013.01); *A61B 5/4866* (2013.01); *A61B 5/742* (2013.01); *A61B 5/7405* (2013.01); *A61B 5/7455* (2013.01); *A61C 7/08* (2013.01); *A61C 8/00* (2013.01); *G01N 21/27* (2013.01); *G01N 21/31* (2013.01); *G01N 33/02* (2013.01); *G09B 19/0092* (2013.01); *H01J 49/0013* (2013.01); *H01J 49/0036* (2013.01); *A61C 5/00* (2013.01); *A61C 5/20* (2017.02); *G01N 2201/12* (2013.01)

(58) Field of Classification Search
CPC .... A61B 5/0031; A61B 5/7455; G01N 21/27; G01N 21/31; G01N 33/02; G01N 2201/12; H01J 49/0036; H01J 49/0013; A61C 7/08; A61C 5/00; A61C 5/20
USPC ................. 340/573.1, 539.1, 539.11, 539.13
See application file for complete search history.

(56) References Cited

U.S. PATENT DOCUMENTS

| | | | |
|---|---|---|---|
| 6,430,450 B1 * | 8/2002 | Bach-y-Rita | A61F 9/08 607/134 |
| 6,735,477 B2 | 5/2004 | Levine | |
| 8,649,543 B2 | 2/2014 | Abolfathi et al. | |
| 8,715,181 B2 | 5/2014 | Brynelsen et al. | |
| 8,753,257 B2 | 6/2014 | Mersky | |
| 9,017,069 B2 | 4/2015 | Boyden et al. | |
| 9,117,363 B2 | 8/2015 | Kimmel | |
| 10,058,283 B2 | 8/2018 | Zerick et al. | |
| 10,321,875 B2 * | 6/2019 | Zerick | A61B 5/682 |
| 2009/0210032 A1 | 8/2009 | Beiski et al. | |
| 2009/0281433 A1 | 12/2009 | Saadat et al. | |
| 2012/0143021 A1 | 6/2012 | Nagar | |
| 2013/0049931 A1 | 2/2013 | Baym et al. | |
| 2013/0203024 A1 | 8/2013 | Dekar | |
| 2013/0253286 A1 | 9/2013 | Fridman | |
| 2014/0152464 A1 | 6/2014 | Smith | |
| 2014/0329192 A1 * | 11/2014 | Kaskoun | A61B 5/682 433/6 |
| 2014/0335469 A1 * | 11/2014 | Boyden | A61B 7/04 433/27 |
| 2015/0272473 A1 | 10/2015 | Zafiroglu et al. | |
| 2015/0290454 A1 * | 10/2015 | Tyler | G06F 3/0383 607/134 |
| 2015/0305671 A1 | 10/2015 | Yoon et al. | |
| 2015/0379238 A1 | 12/2015 | Connor | |
| 2016/0015321 A1 | 1/2016 | Hashemian | |
| 2020/0152312 A1 * | 5/2020 | Connor | G06K 9/00335 |

FOREIGN PATENT DOCUMENTS

| | | |
|---|---|---|
| KR | 20080094139 | 3/2009 |
| KR | 20110138748 A * | 12/2011 |
| WO | WO 2005/115225 A2 | 12/2005 |
| WO | WO 2006/045607 | 5/2006 |
| WO | WO 2009/013371 | 1/2009 |

OTHER PUBLICATIONS

Park, Hangue "A Wireless Magnetoresistive Sensing System for an Intraoral Tongue-Computer Interface." Dec. 6, 2012, pp. 1-15.
Li, Cheng-Yuan "Sensor-Embedded Teeth for Oral Activity Recognition." Sep. 2013, pp. 1-4.

* cited by examiner

DETERMINING FOOD IDENTITIES WITH INTRA-ORAL SPECTROMETER DEVICES

This application is a continuation of U.S. patent application Ser. No. 16/126,611, filed Sep. 10, 2018, now U.S. Pat. No. 10,321,875, which is a continuation of U.S. patent application Ser. No. 15/824,863, filed Nov. 28, 2017, now U.S. Pat. No. 10,070,818, which is a continuation of U.S. patent application Ser. No. 15/092,142, filed Apr. 6, 2016, now U.S. Pat. No. 10,058,283, all of which are herein incorporated by reference in their entirety.

The present disclosure relates generally to determining food compositions, and more particularly, to intra-oral spectrometer devices, methods, computer-readable media, and systems for determining food identities.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
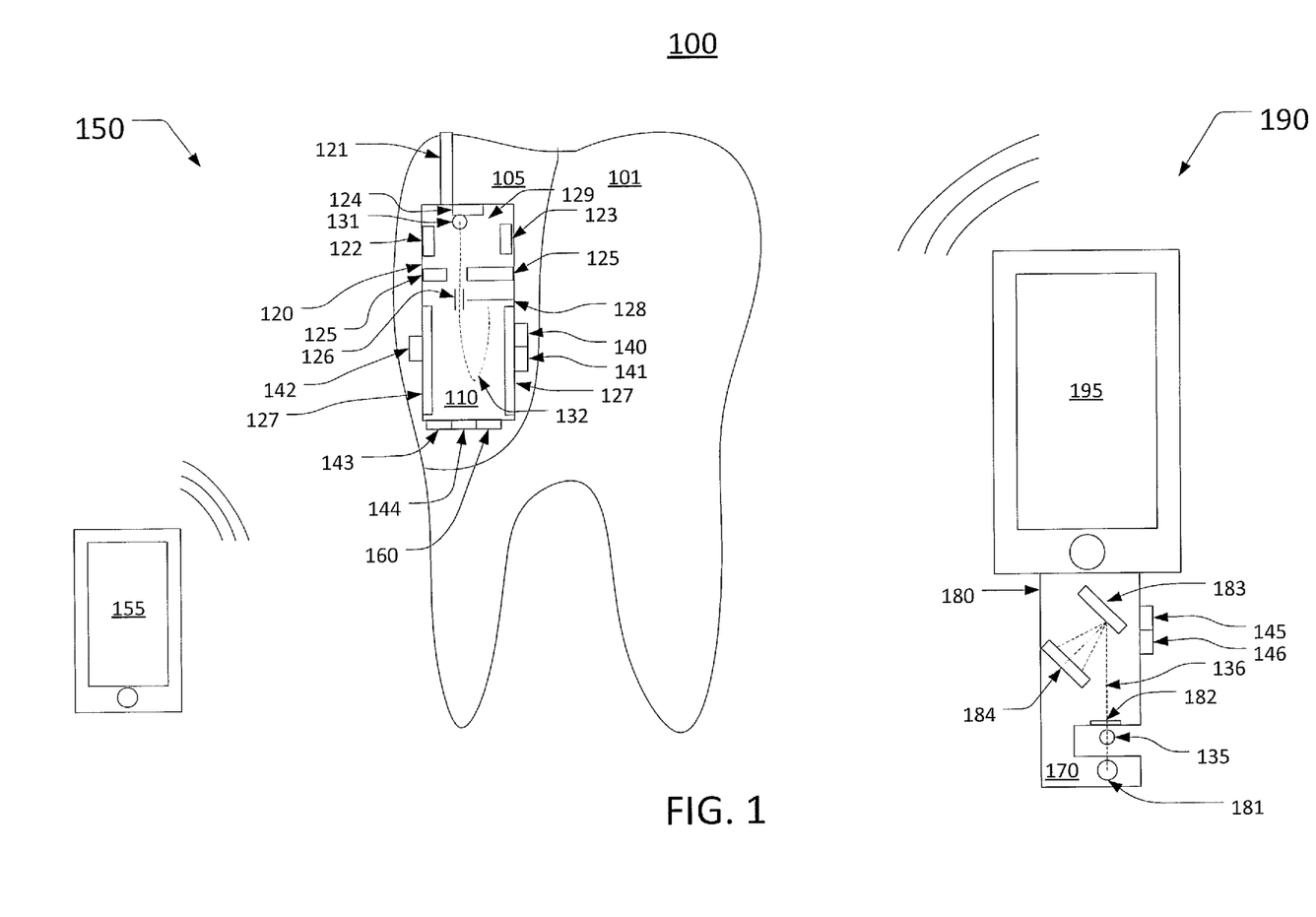
FIG. 1 illustrates example devices and systems related to the present disclosure.

To aid in understanding the present disclosure, FIG. 1 illustrates a first example system 150 and a second example system 190. The system 150 may include an intra-oral device 110 and a wireless device 155 to communicate wirelessly with the intra-oral device 110. In various examples, the wireless device 155 may comprise a cellular telephone, a smartphone, a computing tablet, an Institute of Electrical and Electronics Engineers (IEEE) 802.11 (Wi-Fi) wireless router or a Wi-Fi user device, a Bluetooth device, and so forth. In one example, the wireless device 155 may be deployed in a fixed or substantially fixed location, or may be a mobile device that can be moved by a person or other animal subjects. Accordingly, wireless device 155 may be battery powered, or may receive electrical power from a wired electrical outlet, for instance. In one example, the intra-oral device 110 may be deployed in an oral cavity. For instance, the intra-oral device 110 may be deployed in a dental fixture, such as a crown, a bridge, a retainer, a filling, an implant, or the like. As illustrated in FIG. 1, intra-oral device 110 is deployed in a veneer or filling 105 of a tooth 101. As illustrated in FIG. 1, the intra-oral device 110 may include a spectrometer, e.g., a mass spectrometer 120. Intra-oral device 110 may also include a channel 121 for delivering food samples, such as food sample 131, to the mass spectrometer 120. In one example, the channel 121 may comprise a passive or active microfluidic channel. For instance, the channel 121 may include a valve, a pump, and so forth, for moving food sample 131 from the oral cavity into an ionization chamber 129 of the mass spectrometer 120. In one example, the food sample 131 that is delivered via the channel 121 may comprise gas phase components. In another example, the food sample 131 may comprise liquid phase components, aerosolized components, a combination of liquid and gas phase components, and so on.

As illustrated in FIG. 1, example mass spectrometer 120 may include an ionization source 122, such a coil, a filament, or an electron beam source, an electron trap/collector 123, an ion repeller 124, ion accelerator(s)/focuser(s) 125, a deflector 126, a reflectron 127, and an impact detector array 128. For instance, mass spectrometer 120 may comprise an electron impact ionization (EI)-based time-of-flight (TOF) mass spectrometer. In one example, the ionization chamber 129, the reflectron 127, and other portions of the interior of mass spectrometer 120 may be kept at or near a vacuum state. In one example, food sample 131 may be bombarded with electrons from ionization source 122, which may cause component molecules in food sample 131 to be stripped of electrons, thereby generating positively charged ions. The electrons may be collected by the electron trap/collector 123, while the positively charged ions from food sample 131 may be directed out of the ionization chamber 129 and towards the reflectron 126 by the ion repeller 124, which may comprise a positively charged electrode. The positively charged ions may be accelerated and focused through ion accelerator(s)/focuser(s) 125 before begin deflected by deflector 126 and passing into reflectron 127. The accelerator(s)/focuser(s) 125 may comprise one or more charged rings having a voltage gradient to cause the positive ions to accelerate towards the reflectron 127. Similarly, the reflectron 127 may comprise a stack of ring electrodes for generating an electric field with a gradient to deflect, or "reflect" the ions back towards the accelerator(s)/focuser(s) 125. The deflector 126 may comprise parallel plates with a voltage differential to generate an electric field for deflecting the ions and imparting a velocity to the ions in a direction perpendicular to the direction in which the ions enter the reflectron 127. Due to this deflection, the ions may impact detector array 128 rather than pass back into the ionization chamber 129.

In one example, the detector array 128 may comprise a charge coupled device (CCD), a micro-channel plate detector, a photo-multiplier detector, and so forth. Notably, ions of different mass-to-charge ratios may be imparted with different velocities by the uniform electric field generated by deflector 126. As such, the ions may impact the detector array 128 at different locations. For example, path 132 illustrates an example path that an ion from food sample 131 may take after being accelerated by accelerator(s)/focuser(s) 125, deflected by deflector 126, and reflected by reflectron 127. Thus, different ions with different mass to charge ratios may be detected and differentiated via impact detector array 128.

In accordance with the present disclosure, the food sample 131 may include different molecules comprising proteins, fats, carbohydrates, and so forth. In addition, when ionized via ionization source 122, food sample 131 may generate various ions that are characteristic of the food sample 131. For instance, if the food sample comprises a portion of tofu, it may include a variety of proteins that are characteristic of soybeans. In addition, these proteins may give rise to a set of ions that are indicative of the proteins present in soybeans. Further, these ions may generate a pattern of measurements that are detected at impact detector array 128, based upon the mass-charge ratios of the ions that are generated from the food sample 131. In one example, a mass spectrometer of the same or substantially similar dimensions and configuration as mass spectrometer 120 may be used in-vivo to measure distributions of ion detections for food samples of a variety of common foods. In addition, distributions may be aggregated for foods in a number of different categories, such as shellfish, poultry, leafy vegetables, root vegetables, berries, breads and other wheat-based baked foods, and so forth. Similarly, measurements for sets of foods having similar characteristics, e.g., high fat content, high sugars, and so forth, may be obtained to generate distribution patterns that are indicative of high fat foods, high sugar foods, and so forth. In accordance with the present disclosure, any such distributions may be referred to as a "food signature," which may be indicative of a composition or an ingredient of a type of food. Thus, a food signature indicative of an identity of a food may be associated with a particular food, a food category, or a food characteristic. In other words, in one example the "identity" of the sample of food may comprise the actual food name, e.g., an orange or a banana, whereas in another example the "identity" of the sample of food may comprise the food category of a "fruit" category, or a "meat" category, whereas in yet another example the "identity" of the sample of food may comprise the food characteristics of: "sugary," "sour," "acidic," and the like.

In accordance with the present disclosure, a pattern detected from food sample 131 via impact detector array 128 of mass spectrometer 120 may be compared to known food signatures to determine an identity of a food from which the food sample was extracted. In one example, the intra-oral device 110 may include a processor 140 and a computer-readable medium 141 storing instructions which, when executed by processor 140 may cause processor 140 to perform operations for determining an identity of a food, in accordance with the present disclosure. For instance, the instructions stored by computer-readable medium 141 may cause the processor to perform operations as described in greater detail below in connection with the example method 300 of FIG. 3. In one example, the intra-oral device 110 may also include a transceiver 142. For instance, transceiver 142 may comprise a wireless transceiver, e.g., for IEEE 802.11, Bluetooth, and/or Bluetooth Low Energy (BLE) communications, and the like. In one example, processor 140 may obtain the measurements from impact detector array 128 of mass spectrometer 120 and transmit the measurements to wireless device 155 via transceiver 142. In one example, wireless device 155 may be tasked with comparing the measurements to a plurality of food signatures, and determining an identity (or more specifically a composition) of food in the oral cavity based upon the measurements. For instance, wireless device 155 may store a database of food signatures obtained in the manner above. In one example, wireless device 155 may also present feedback based upon the identity or the composition of food that is determined. For example, the wireless device 155 may present visual feedback on a display of the wireless device 155, audio feedback via a speaker of the wireless device 155, and so forth.

In one example, the wireless device 155 may present feedback in the form of an instruction, or instructions to the intra-oral device 110. For example, intra-oral device 110 may include a feedback unit 143 for generating an output that is detectable by a human or animal subject associated with the intra-oral device 110. For instance, unit 143 may deliver a mild electrical stimulation or a vibration that may be perceived by the subject. To illustrate, wireless device 155 may be configured to transmit instructions to processor 140 of intra-oral device 110 when a particular food, food category, or food characteristic is detected. For instance, if the wireless device 155 determines that the measurements match a food signature of crab, lobster, or other shellfish, and if the subject has a shellfish allergy, the wireless device 155 may send an instruction to cause the processor to generate an electrical stimulation via the feedback unit 143. The electrical stimulation may serve as a warning to the subject that the composition of the food is potentially harmful. In still another example, the measurements may match a food signature indicating a high sugar content. If the subject is a diabetic, for example, the wireless device 155 may also generate feedback via the wireless device 155 itself or via the processor 140 and feedback unit 143 of intra-oral unit 110 to warn the subject.

In one example, intra-oral device 110 may be powered by a rechargeable battery 144 that may be charged via induction coupling or via a piezoelectric transducer (not shown) that may be generate a current when a subject's jaw is moved during the course of everyday experiences. In addition, intra-oral device 110 may include a sensor 160 (e.g., an analog sensor), which may comprise a current sensor, moisture sensor, or a pH sensor for detecting a condition that may be indicative of salivation and thus eating. In one example, the sensor 160 may be used to determine when to active and deactivate measurements via the mass spectrometer 120 in order to conserve power and to prevent unnecessary wear of the components of intra-oral unit 110. For instance, if the sensor 160 comprises a moisture sensor, an elevated moisture level may be indicative of salivation, and hence eating. Accordingly, in one example, mass spectrometer 120 may be activated when the sensor 160 detects that a moisture level exceeds a threshold. In another example, if the sensor 160 comprises a pH sensor, a low pH level may be indicative of an elevated saliva level (or an acidic food), and hence eating. Thus, in one example, mass spectrometer 120 may be activated when the sensor 160 detects that a pH level exceeds a threshold. In still another example, if the sensor 160 comprises a current sensor, a current above a threshold may also indicate an elevated saliva level or a presence of a salty food, and hence eating. Thus, in one example, mass spectrometer 120 may be activated when the sensor 160 detects that a current level exceeds a threshold. In one example, the reading of sensor 160 alone may be used to wake the intra-oral device 110 and activate measurements via the mass spectrometer 120. However, in another example, the reading of sensor 160 exceeding a threshold plus a jaw movement being detected (e.g., via a piezoelectric transducer) may be used as a combination of conditions which, when satisfied, will trigger the waking or operation of the intra-oral device 110 and the measurements via mass spectrometer 120.

FIG. 1 also illustrates a second example system 190. The system 190 may include an intra-oral device 170 and a mobile device 195 coupled to and in communication with the intra-oral device 170. For instance, intra-oral device 170 and mobile device 195 may share any type of wired or plug-in connection such as uniform serial bus (USB) interface, a high definition multimedia interface (HDMI), and so forth, for conveying electronic communications between the respective components. In one example, intra-oral device 170 may also receive electrical power from mobile device 195 via the same or a different connection. In various examples, the mobile device 195 may comprise a cellular telephone, a smartphone, a computing tablet, a wireless device, e.g., IEEE 802.11 device, or the like. In one example, the intra-oral device 170 may be for deployment in an oral cavity. For instance, the intra-oral device 170 may be inserted into a subject's mouth after chewing a food. Intra-oral device 170 may comprise a spectrometer, e.g., spectrophotometer 180. In one example, the spectrophotometer 180 may comprise a photodiode array spectrophotometer.

As illustrated, in FIG. 1, spectrophotometer 180 may include a light source 181, e.g., a broadband, multi-wavelength and/or multi-band light source, such as a light emitting diode (LED) array. Spectrophotometer 180 may also include an aperture 182, a diffraction grating 183, and a detector array 184. In one example, spectrophotometer 180 may operate as follows. Light from light source 181 may be directed toward a food sample 135. The food sample 135 may comprise gas phase components, liquid phase components, aerosolized components, a combination of liquid and gas phase components, and so on. The food sample 135 may absorb certain wavelengths of light, while reflecting/transmitting other wavelengths of light in response to the illumination from light source 181. The reflected/transmitted wavelengths of light may pass through aperture 182 to generate a beam of light 136 directed toward diffraction grating 183. The diffraction grating 183 may reflect different wavelengths in the beam of light 136 toward the detector array 184, but at different angles to generate an illumination pattern on the detector array 184. The detector array 184 may comprise a photodiode array or a CCD, for example. Respective electric currents may be generated when light of different wavelengths impinges upon different portions of the detector array 184. As such, the detector array 184 may measure the illumination pattern that is indicative of the reflectance and/or transmittance spectra of the food sample 135. In one example, the detector array 184 may measure the illumination pattern over a time interval such that different molecules or other components present in the food sample 135 may be illuminated with light from light source 181 and have the respective reflectance and/or transmittance spectra appear in the illumination pattern at detector array 184.

In one example, a spectrophotometer of the same or substantially similar dimensions and configuration as spectrophotometer 180 may be used in-vivo to generate a plurality of food signatures. Such food signatures may be similar to those described above in connection with mass spectrometer 120 of the first example system 150. For instance, distributions of illumination patterns for food samples may be measured for a variety of common foods. In addition, distributions may be aggregated for foods of a similar category, such as shellfish, poultry, leafy vegetables, root vegetables, berries, breads and other wheat-based baked foods, and so forth. Similarly, measurements for sets of foods having similar characteristics, e.g., high fat content, high sugars, and so forth, may be obtained to generate distribution patterns that are indicative of high fat foods, high sugar foods, and so forth.

In accordance with the present disclosure, a pattern detected from food sample 135 via detector array 184 of spectrophotometer 180 may be compared to known food signatures to determine a composition of food from which the food sample 135 was extracted. In one example, the intra-oral device 170 may include a processor 145 and a computer-readable medium 146 storing instructions which, when executed by processor 145 may cause processor 145 to perform operations for determining a composition or ingredient of a food, in accordance with the present disclosure. For instance, the instructions stored by computer-readable medium 146 may cause the processor 145 to perform operations as described in greater detail below in connection with the example method 300 of FIG. 3. In one example, processor 145 may obtain the measurements from detector array 184 of spectrophotometer 180 and transmit the measurements to mobile device 195. In one example, mobile device 195 may be tasked with comparing the measurements to a plurality of food signatures, and determining a composition of food in the oral cavity based upon the measurements. For instance, mobile device 195 may store a database of food signatures obtained in the manner above. In one example, mobile device 195 may also present feedback based upon the composition of food that is determined. For example, the mobile device 195 may present visual feedback on a display of the mobile device 195, audio feedback via a speaker of the mobile device 195, and so forth.

It should be noted that system 150 and system 190 are just two example systems that include an intra-oral device and a mobile device for determining a composition of a food, and that various additional systems and configurations are possible in accordance with the present disclosure. For instance, in an alternative configuration, mass spectrometer 120 may utilize electrospray ionization (ESI). For example, the food sample 131 may be injected in liquid form into the mass spectrometer 120 and ionized in an electric field before passing through ion accelerator(s)/focuser(s) 125. In still other examples, the mass spectrometer 120 may comprise an ion-trap mass spectrometer, a quadrupole mass spectrometer, and so forth. As such, in various examples mass spectrometer 120 may include alternative or additional components such as a micro-heater to vaporize food sample 131, e.g., if transported into mass spectrometer 120 in liquid form via channel 121, a laser source, e.g., for matrix-assisted laser desorption ionization (MALDI) TOF mass spectrometry, and so on. In another example, transceiver 142 may be substituted with a transmitter and the feedback unit 143 omitted. For instance, any notifications to the subject regarding food compositions that are determined may be provided via the mobile unit 155.

Similarly, in another example, spectrophotometer 180 may comprise a monochromator, with light source 181 comprising a monochromatic light source, for example. In another example, intra-oral device 170 may also include a feedback unit similar to feedback unit 143 of the intra-oral device 110 of the system 150. In another example, intra-oral device 170 may have a separate power source, e.g., a disposable or rechargeable battery, rather than receiving electrical power from mobile device 195. In another example, intra-oral device 170 may also include an analog sensor, similar to analog sensor 160 of intra-oral device 110 of the system 150 for determining when to activate spectrophotometer 180. In still another example, the spectrophotometer 180 and the mass spectrometer 120 may be substituted for one another. For instance, intra-oral device 110 embedded in dental fixture 105 may instead utilize a spectrophotometer for measuring properties of the food sample 131, while intra-oral device 170 may utilize a mass spectrometer to measure properties of the food sample 135. Thus, these and other modifications are all contemplated within the scope of the present disclosure.

It should be further noted that examples of the present disclosure that are embedded in dental fixtures, such as intra-oral unit 110 in dental fixture 105, are not limited to human subjects, but may be broadly applicable to any animal subjects. For instance, miniature TOF mass spectrometers are claimed to have been demonstrated at the order of 30 mm×30 mm×5 mm or less. Similarly, photodiode array spectrophotometers are claimed to have been demonstrated at 45 mm×25 mm×10 mm and 22 mm×35 mm×14 mm, respectively. Notably, an adult elephant may have molar teeth greater than 20 cm long and 7 cm wide and weighing more than 4-5 kg. Elephant molars may be compared to the size of a brick, for example. Horse teeth may also be up to 12 cm long. Although most of the tooth may be situated below the gum line, equine tooth extraction is a routine occurrence. As such, a removed tooth may be replaced by a fixture that may include a spectrometer device in accordance with the present disclosure. In veterinary subjects, measurements of properties of food samples may then be transmitted to a mobile device of a caregiver, such as a zookeeper or veterinarian, or a mobile device strapped to the animal subjects, for example.

Figure 2:
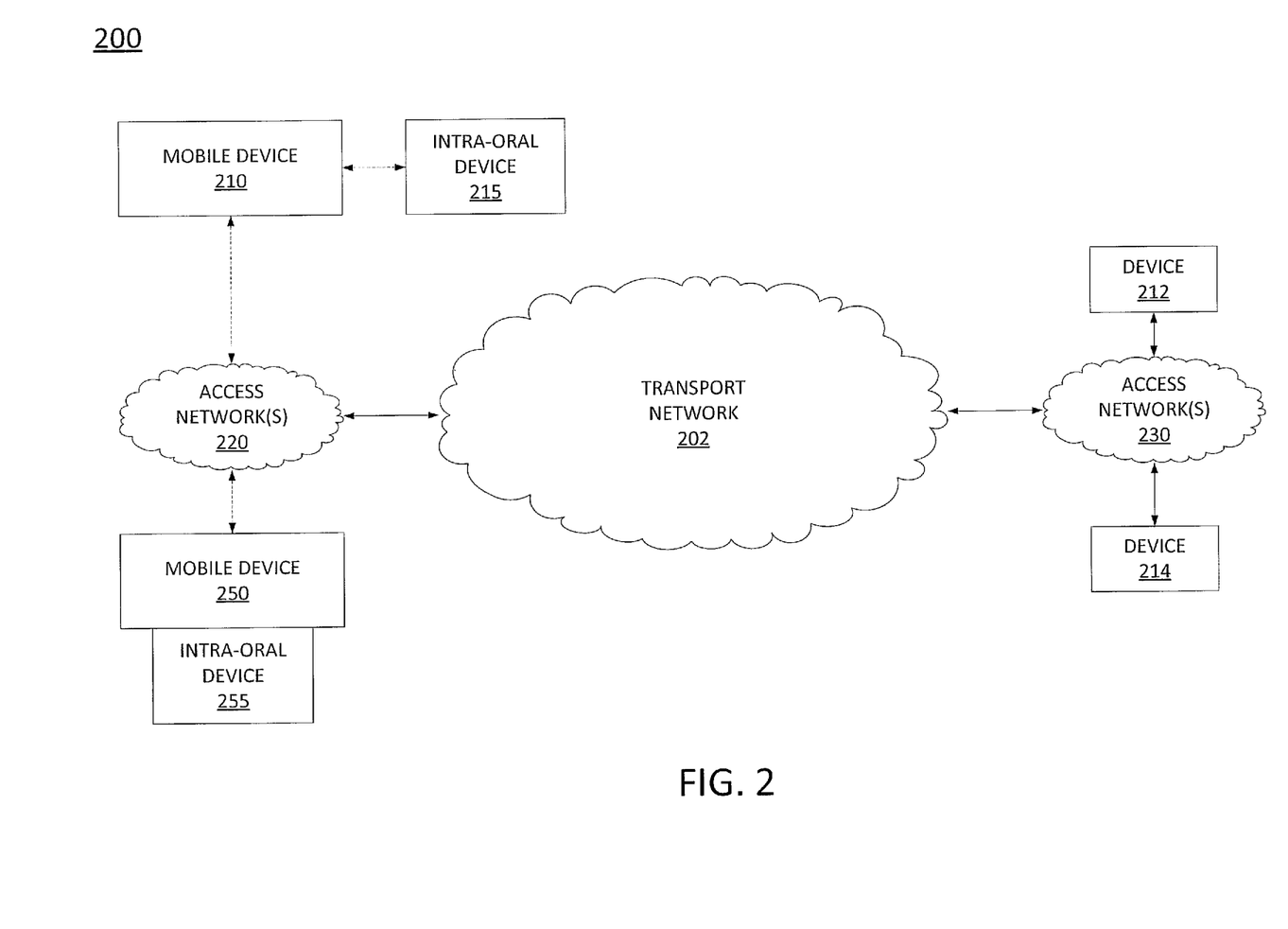
FIG. 2 illustrates an example network related to the present disclosure.

FIG. 2 is a block diagram depicting one example of a network or communications system 200 related to examples of the present disclosure. The overall communications system 200 may include any number of interconnected networks which may use the same or different communication technologies, such as a traditional circuit switched network (e.g., a public switched telephone network (PSTN)) or a packet network such as an Internet Protocol (IP) network (e.g., an IP Multimedia Subsystem (IMS) network), a multiprotocol label switching (MPLS network), a frame relay network, an asynchronous transfer mode (ATM) network, a wireless network, a cellular network (e.g., 2G, 3G, and the like), a long term evolution (LTE) network, a software-defined network, and so forth. It should be noted that an IP network is broadly defined as a network that uses Internet Protocol to exchange data packets.

As illustrated in FIG. 2, system 200 may include a transport network 202. In one example, the transport network 202 may be operated by a telecommunications service provider that is providing one or more telecommunications services such as telephony services, data services, Internet access services, multimedia content delivery services and the like. In one embodiment, the transport network 202, broadly a "communications network," may be in communication with one or more access networks 220 and 230. The access networks 220 and 230 may include a wireless access network (e.g., an IEEE 802.11/Wi-Fi network and the like), a cellular access network, a PSTN access network, a cable access network, a digital subscriber line (DSL) network, a metropolitan area network (MAN), other types of wired access networks, an Internet service provider (ISP) network, and the like. In one embodiment, the access networks 220 and 230 may all be different types of access networks, may all be the same type of access network, or some access networks may be the same type of access network and other may be different types of access networks. The transport network 202 and the access networks 220 and 230 may be operated by different service providers, the same service provider or a combination thereof. Alternatively, or in addition, access networks 220 and 230 may represent corporate, governmental or educational institution LANs, a home/residential LAN, and the like.

In the example of FIG. 2, either or both of the intra-oral devices 215 and 255 may comprise an intra-oral device as illustrated in FIG. 1 and as described above, e.g., including at least a spectrometer and a processor for communicating externally with a mobile device. In one example, intra-oral devices 215 and 255 may each comprise a computing system, such as computing system 500 depicted in FIG. 5, and may be configured to provide one or more functions for determining a composition or ingredient of a food, as described in connection with the example method 300 of FIG. 3, and/or as described elsewhere herein. It should be noted that "configuring" an electrical device may comprise the loading of instructions or machine readable codes onto the electrical device. Said another way, one or more electrical signals can be applied to the electrical device to configure the device to perform one or more described functions. Furthermore, it should be noted that "configuring" an electrical-mechanical device may comprise the loading of instructions or machine readable codes onto the electrical-mechanical device and/or implementing structural features (e.g., of appropriate size, shape and material) to bring about one or more described electrical and/or mechanical functions.

As illustrated in FIG. 2, the intra-oral device 255 may plug-into or may be cable-connected to the wireless device 250 for communicating electronic data between the respective devices. Thus, intra-oral device 255 may include a Peripheral Component Interface express (PCIe) transceiver (which may be referred to as a "PHY," a Small Component Serial Interface (SCSI) transceiver, or the like. In this regard, wireless device 250 may include a complementary transceiver for using a same type of communication interface as the intra-oral device 255. Intra-oral device 255 may also receive electrical power from the wireless device 250 via the same connection or via a separate connection. For instance, intra-oral device 255 may measure reflectance/transmittance spectra or an illuminance pattern (e.g., for a photodiode array spectrophotometer) or an ion distribution (e.g., for a mass spectrometer) of a food sample using electrical power from wireless device 250. In addition, intra-oral device 255 may convey the measurements to the wireless device 250 via the connection therebetween. In one example, wireless device 250 may store a plurality of food signatures for comparison to the measurements obtained from intra-oral device 255 and for determining a food composition based upon the comparison. In one example, wireless device 250 may generate feedback based upon a food composition that may be determined. The feedback may comprise an output via the mobile device 250 or may be in the form of instructions to the intra-oral device 255, e.g., as described above. In one example, wireless device 250 may comprise a mobile device, such as a cellular telephone, a smartphone, a wireless device, such as Wi-Fi user device, a Bluetooth device, and so forth. Accordingly, wireless device 250 may communicate with other devices via a wireless connection with one or more components of access networks 220, for example.

As illustrated in FIG. 2, intra-oral device 215 may be in wireless communication with a wireless device 210. For instance, intra-oral device 215 may include a wireless transceiver, e.g., for IEEE 802.11, Bluetooth, and/or BLE communications, and the like. In addition, wireless device 210 may include a similar transceiver for receiving communications from and transmitting communications to intra-oral device 215. Wireless device 210 may comprise a cellular telephone, a smartphone, a wireless device, e.g., an Wi-Fi router or a Wi-Fi user device, a Bluetooth device, and so forth. The wireless device 210 may be deployed in a fixed or substantially fixed location, or may be a mobile device that can be moved by a person or other subject. In one example, intra-oral device 215 may measure reflectance/transmittance spectra or an illuminance pattern (e.g., for a photodiode array spectrophotometer) or an ion distribution (e.g., for a mass spectrometer) of a food sample and convey the measurements to the mobile device 210 via the wireless connection therebetween. In one example, intra-oral device 215 may be powered by a rechargeable battery that may be charged via induction coupling or via a piezoelectric transducer that may generate a current when a subject's jaw is moved during the course of everyday experiences. In one example, wireless device 210 may store a plurality of food signatures for comparison to the measurements obtained from intra-oral device 215 and for determining a food composition based upon the comparison. In one example, wireless device 210 may generate feedback based upon a food composition that may be determined. The feedback may comprise an output via the wireless device 210 or may be in the form of instructions to the intra-oral device 215, e.g., as described above.

In one example, transport network 202 and access networks 220 and 230 may transmit and receive data communications between intra-oral devices 215 and 255, wireless devices 210 and 250, and devices 212 and 214 relating to determining food compositions in accordance with the present disclosure. In one example, devices 212 and 214 may each comprise a mobile device, a cellular smart phone, a laptop computer, a tablet computer, a desktop computer, a smart television, a server, a cluster of such devices, and the like. For example, devices 212 and 214 may comprise remote monitoring devices that may be used by doctors, nurses, clinicians, zookeepers, veterinarians, and the like to monitor food intake by one or more subjects. In one example, devices 212 and 214 may each comprise a computing system or server, such as computing system 500 depicted in FIG. 5, and may be configured to provide one or more functions for determining a composition or ingredient of a food, as described herein. For instance, devices 212 and 214 may provide remote monitoring and administration of wireless device 210, wireless device 250, intra-oral device 215, and/or intra-oral device 255.

The monitoring may include receiving notifications from wireless devices 210 and 250 regarding a detection of a food composition. For instance, device 212 may comprise a server that tracks a food intake of a monitored subject over a period of time, e.g., over the course of a day, a week, a month, etc. As such, either or both of wireless devices 210 and 250 may report detection of food compositions to device 212, e.g., when detected, on a periodic basis, or when a connection to device 212 via access networks 220, access networks 230, and transport network 202 is available, and so forth.

Alternatively, or in addition, either or both of wireless devices 210 and 250 may report when a particular composition of a food is detected. For instance, if a subject is lactose intolerant and the measurements of intra-oral device 215 are indicative of the ingestion of a lactose containing diary item by the subject (e.g., as determined by the wireless device 210), the wireless device 210 may report this condition to device 212 to record the event. Alternatively, or in addition, wireless device 210 may transmit a notification to device 214, which may comprise a mobile device of a party that is responsible for the subject. For example, many adult mammals are lactose intolerant. However, a visitor to a zoo may inadvertently drop a milk carton where it is accessible to one of the zoo animals, which may then proceed to ingest the milk. Accordingly, the zoo's veterinarian may wish to know about such an event with respect to a subject that may be on a strict diet and/or that is recovering from an illness, and so forth.

In another example, either or both of wireless devices 210 and 250 may not store food signatures, or may store an incomplete set of food signatures, while device 212, for instance, may store a full set of food signatures. Thus, in one example, if wireless device 250 is not configured to compare measurements from intra-oral device 255 to food signatures, or if it cannot match a particular set of measurements to any food signature, wireless device 250 may convey the measurements to device 212 via access networks 220, transport network 202, and access networks 230. In turn, device 212 may then compare the measurements to a plurality of food signatures and determine a composition of the food based upon the comparisons. In addition, device 212 may return a result to wireless device 250, and/or may return an instruction to generate a feedback via wireless device 250 and/or intra-oral device 255.

In still another example, device 214 may be used by a responsible party to update a food signature watch list for one of the wireless device 210 or wireless device 250, and/or for intra-oral device 215 or intra-oral device 255. For instance, if a subject associated with intra-oral device 215 is on a particular diet for two weeks, the responsible party may monitor the subject for compliance with the diet during this period and receive warnings at device 214 of any deviations based upon the measurements of intra-oral device 215. However, after this time period has passed, the subject may be permitted to resume a less restrictive diet and the responsible party may no longer wish to receive notifications regarding particular foods on the watch list. Thus, the watch list implemented on wireless device 210 for intra-oral device 215 may be changed or canceled via a further instruction from device 214. In still another example, device 214 may be used to send instructions to intra-oral device 215 via wireless device 210. The instructions may be for reconfiguring the intra-oral device 215 to have a different sleep/wake threshold for making measurements, to set a different period for sending measurements to wireless device 210, to reset a processor, e.g., where recent measurement data may be indicative of a malfunction, and so forth.

It should be noted that the system 200 has been simplified. In other words, the system 200 may be implemented in a different form than that which is illustrated in FIG. 2. For example, the system 200 may be expanded to include other network elements (not shown) such as border elements, routers, switches, policy servers, security devices, gateways, a content distribution network (CDN), and the like, without altering the scope of the present disclosure. Similarly, system 200 may omit various elements, substitute elements for devices that perform the same or similar functions and/or combine elements that are illustrated as separate devices. For example, device 212 or device 214 may comprise functions that are spread across several devices that operate collectively as a remote monitoring device. For instance, a remote monitoring device may comprise a virtual machine operating on one or more physical host devices in same location or distributed among several physical locations. In another example, device 212 or device 214 may alternatively be deployed in network 202. In addition, although two access networks 220 and 230, two devices 212 and 214, two wireless devices 210 and 250, and two intra-oral devices 215 and 255 are illustrated in FIG. 2, it should be understood that any number of access networks and devices may connect to the transport network 202.

Figure 3:
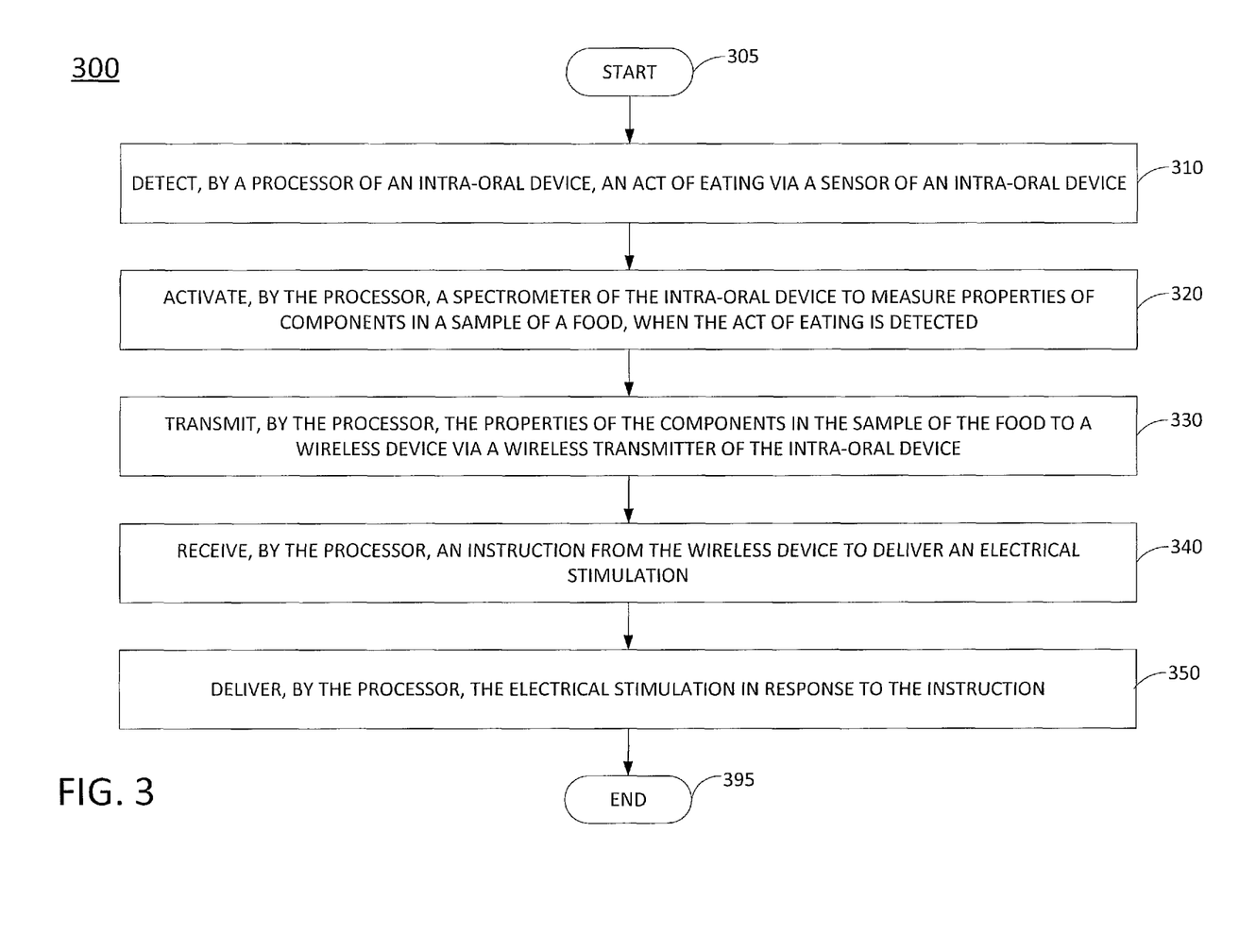
FIG. 3 illustrates a flowchart of an example method for determining a composition of a food, in accordance with the present disclosure.

FIG. 3 illustrates a flowchart of an example method 300 for determining a composition of a food, in accordance with the present disclosure. In one example, steps, functions and/or operations of the method 300 may be performed by an intra-oral device. Alternatively, or in addition, the steps, functions, or operations of method 300 may be performed by a computing device or system 500, and/or processor 502 as described in connection with FIG. 5 below. For illustrative purposes, the method 300 is described in greater detail below in connection with an example performed by a processor, such as processor 502. For example, the processor may comprise a processor of an intra-oral device as described herein.

The method begins in step 305 and proceeds to step 310. At step 310, the processor detects an act of eating via a sensor of the intra-oral device. For example, the sensor may comprise a moisture sensor to detect a moisture level that exceeds a threshold, a pH sensor to detect a pH that exceeds a threshold, a pressure sensor to detect a certain amount of applied pressure representative of chewing of a food item, or a current sensor to detect an electrical current that exceeds a threshold. Any of these conditions may be indicative of salivation associated with the act of eating. A low pH, e.g., below a threshold, such as below 5.6, may also be indicative of an ingestion of an acidic food, such as a citrus fruit, coffee, and so forth. Conversely a high pH, e.g., above a threshold, e.g., above 7.9, may be indicative of ingestion of an alkaline food, e.g., milk, banana, squash, and so on. In one example, the intra-oral device may also be powered by a rechargeable battery that is charged via a motion of a jaw or mouth activating a piezoelectric transducer, or using a similar arrangement. Accordingly, in one example, the act of eating may be detected at step 310 when a sensor measurement exceeds a threshold and when a current from the piezoelectric transducer is also present.

At step 320, the processor activates a spectrometer of the intra-oral device to measure one or more properties of one or more components in a sample of a food, e.g., in response to detecting the act of eating at step 310. In one example, the spectrometer may comprise a mass spectrometer and the properties may comprise ion distributions measured at an impact detector array. In another example, the spectrometer may comprise a spectrophotometer and the properties may comprise reflectance/transmittance spectra, e.g., based upon an illumination pattern measured, or detected at a photodiode array, a CCD array, or the like. In one example, the intra-oral device (including the processor) may be embedded in a dental fixture of a subject.

At step 330, the processor transmits the properties of the components in the sample of the food to a wireless device via a wireless transmitter of the intra-oral device. The wireless device may comprise a cellular telephone, a smartphone, a computing tablet, a wireless device, e.g., a wireless router, a wireless user device, a Bluetooth device, and so forth. In one example, the wireless device may be deployed in a fixed or substantially fixed location, or may be a mobile device that can be moved by a person or other subjects.

At step 340, the processor receives an instruction from the wireless device to deliver a stimulation, e.g., an electrical stimulation. For example, the wireless device may store a plurality of food signatures to which the properties of the components in the sample of the food may be compared. If there is a match, this may indicate that the sample of the food is associated with a particular identifiable food, a food category, or a food characteristic. In one example, the plurality of food signatures may comprise a food signature watch list. For example, a subject may have a peanut allergy. Accordingly, the food signature watch list may include a food signature for "peanuts" for the wireless device to specifically detect when the composition of the food includes traces of peanut. In addition, in one example, the wireless device may transmit an instruction to deliver feedback via the intra-oral device, e.g., to warn the subject of the detection of a potentially harmful food. The feedback may comprise a mild electrical stimulation to the subject.

At step 350, the processor delivers the stimulation, e.g., in response to the instruction received at step 340. For instance, the processor may generate a current between electrodes that are in contact with a portion of the oral cavity of the subject such as a tooth or a portion of the subject's gum, inner cheek, or a tactile sensation, and so forth. Following step 350, the method 300 proceeds to step 395 where the method ends.

Figure 4:
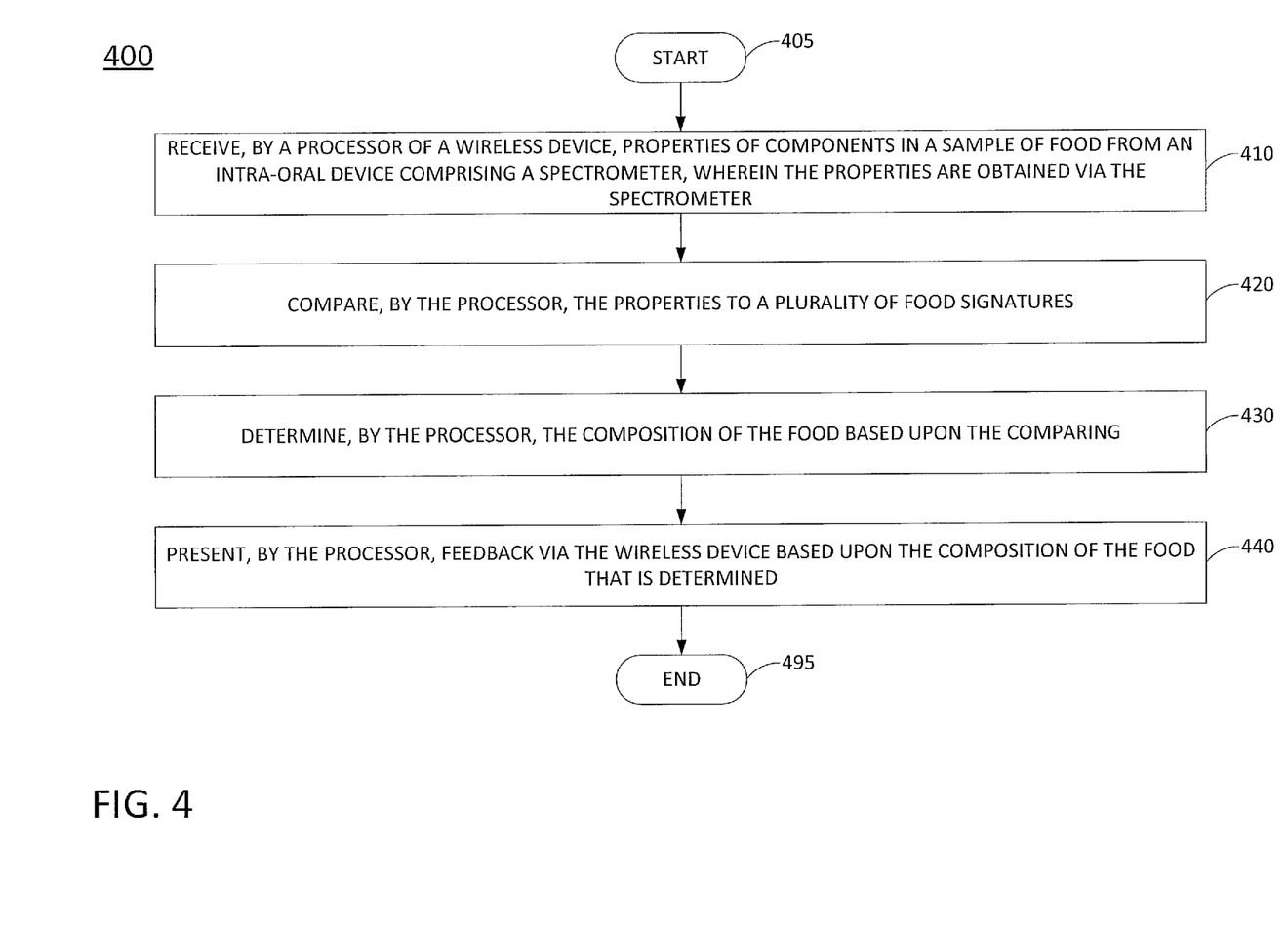
FIG. 4 illustrates a flowchart of an additional example method for determining a composition of a food, in accordance with the present disclosure.

FIG. 4 illustrates a flowchart of an additional example method 400 for determining a composition of a food, in accordance with the present disclosure. In one example, steps, functions and/or operations of the method 400 may be performed by a wireless device that is in communication with an intra-oral device. Alternatively, or in addition, the steps, functions, or operations of method 400 may be performed by a computing device or system 500, and/or processor 502 as described in connection with FIG. 5 below. For illustrative purposes, the method 400 is described in greater detail below in connection with an example performed by a processor, such as processor 502. For example, the processor may comprise a processor of a wireless device and/or a monitoring device as described herein.

The method begins in step 405 and proceeds to step 410. At step 410, the processor receives one or more properties of one or more components in a sample of food from an intra-oral device that includes a spectrometer, where the properties are obtained via the spectrometer. In one example, the spectrometer may comprise a mass spectrometer to measure ion distributions at an impact detector array. In another example, the spectrometer may comprise a spectrophotometer to measure reflectance/transmittance spectra, e.g., based upon an illumination pattern detected at a photodiode array, a CCD array, or the like. In one example, the intra-oral device may be embedded in a dental fixture of a subject and the processor may receive the properties of components in a sample of food via a wireless transmission from the intra-oral device. In one example, the intra-oral device may be coupled to a wireless device, e.g., a mobile device, and may be for insertion into an oral cavity of a subject to obtain the sample of the food. In one example, the wireless device may contain the processor. In such an example, the processor may receive the properties of components in a sample of food via a communication over a wired connection from the intra-oral device.

At step 420, the processor compares the one or more properties of the one or more components in the sample of the food to a plurality of food signatures. For example, the wireless device may store a plurality of food signatures to which the properties of the components in the sample of the food may be compared. In one example, the plurality of food signatures may comprise a food signature watch list, as described above.

At step 430, the processor determines an identity of the sample of food based upon the comparing. For example, if the one or more properties of the one or more components in the sample of the food match a food signature, this may indicate that the sample of the food is associated with or representative of a particular identifiable food, a food category, or a food characteristic. For instance, if the properties of the components in the sample of the food match a food signature for "peanuts," the composition of the food may be determined to be "peanuts." It should be noted that in some instances the properties of the components in the sample of the food may match more than one signature. For example, there may be a match for a food signature of "peanuts" as well as a match for "high fat content" if the subject is eating peanut butter. Thus, the composition of the food may be determined to include at least the identifications of "peanuts" and "high fat content."

At step 440, the processor presents a feedback based upon the identity of the sample of food that is determined. For example, the processor may present a visual output on a display screen of a device of the processor indicating the identity of the sample of food that is determined. The processor may also present additional information related to the composition of the food that is determined, such as nutritional information regarding the food, suggestions for healthier alternatives, and so forth. Alternatively, or in addition, the visual output may comprise an activation of a particular color light, a blinking light, or the like, to indicate that a potentially harmful food has been detected, for example. The processor may also present an audio output via a speaker of the device of the processor. For instance, an audio output may indicate the composition of the food that is determined. Alternatively, or in addition, the audio output may comprise a warning sound, such as a beep, a siren, or the like, to indicate that a potentially harmful food has been detected, for example.

In one example, the feedback may be for a subject associated with the intra-oral device. In another example, the feedback may be for a party that is responsible for the subject, e.g., a doctor, a dentist, a dietician, a veterinarian, and so forth. In this regard, it should be noted that the processor may be deployed in a variety of devices, such as a wireless device in wireless communication with the intra-oral device, or a device that is remote from the intra-oral device, where the intra-oral device, and/or a wireless device associated with the intra-oral device is accessible over one or more communication networks. Thus, the feedback may be presented via any such device in which the processor is deployed or which may generate an output based upon an instruction from the processor. In still another example, the feedback may comprise an instruction to the intra-oral device to deliver an electrical stimulation. For instance, the intra-oral device may include electrodes that are in contact with a portion of the oral cavity of the subject, such as a tooth or a portion of the subject's gum, inner cheek, and so forth, to deliver a mild electrical stimulation, or a tactile sensation, e.g., a vibrating sensation. Following step 440, the method 400 proceeds to step 495. At step 495, the method 400 ends.

It should be noted that although not specifically specified, one or more steps, functions or operations of the method 300 or the method 400 may include a storing, displaying and/or outputting step as required for a particular application. In other words, any data, records, fields, and/or intermediate results discussed in the respective methods can be stored, displayed and/or outputted to another device as required for a particular application. Furthermore, steps or blocks in FIGS. 3 and 4 that recite a determining operation or involve a decision do not necessarily require that both branches of the determining operation be practiced. In other words, one of the branches of the determining operation can be deemed as an optional step. In addition, one or more steps, blocks, functions, or operations of the above described method 300 or method 400 may comprise optional steps, or can be combined, separated, and/or performed in a different order from that described above, without departing from the example embodiments of the present disclosure. For example, the method 400 may be expanded to further include: receiving instructions from a remote device to implement a food signature watch list, to implement particular types of feedback, to transmit a reset instruction to an intra-oral device, to pair with a different intra-oral device, and so forth, transmitting the composition(s) of food(s) that are determined to a remote device for data aggregation, notifying a responsible party that is remote from the subject and/or from the device that includes the processor of the composition(s) of food(s) that are determined, and so on.

Figure 5:
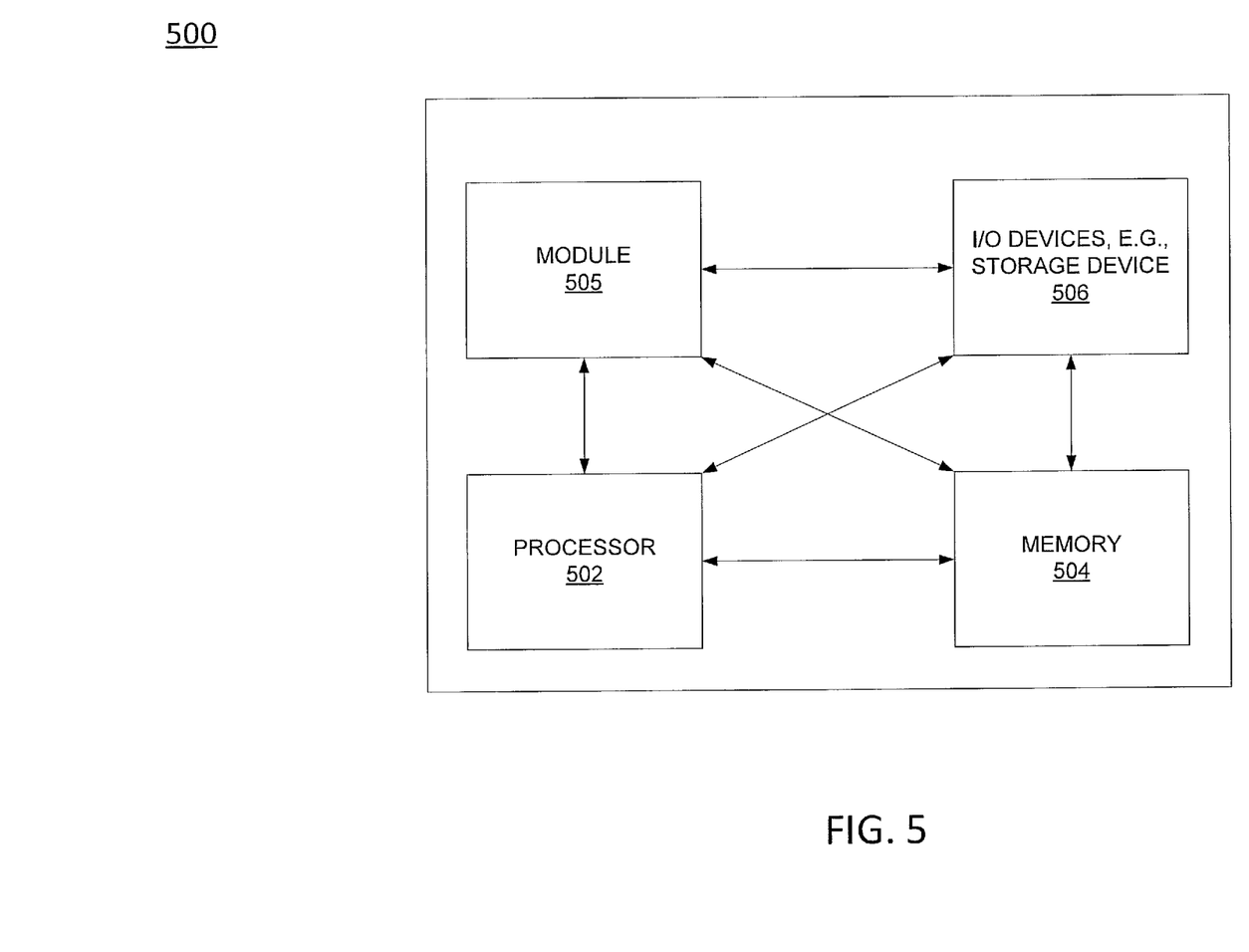
FIG. 5 illustrates an example high-level block diagram of a computer specifically programmed to perform the steps, functions, blocks, and/or operations described herein.

FIG. 5 depicts a high-level block diagram of a computing device suitable for use in performing the functions described herein. As depicted in FIG. 5, the system 500 comprises one or more hardware processor elements 502 (e.g., a central processing unit (CPU), a microprocessor, or a multi-core processor), a memory 504 (e.g., random access memory (RAM) and/or read only memory (ROM)), a module 505 for determining a composition of a food, and various input/output devices 506 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computing device may employ a plurality of processor elements. Furthermore, although only one computing device is shown in the figure, if the method 300 or the method 400 as discussed above is implemented in a distributed or parallel manner for a particular illustrative example, i.e., the steps of the method, or the entire method is implemented across multiple or parallel computing device, then the computing device of this figure is intended to represent each of those multiple computing devices.

Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable gate array (PGA) including a Field PGA, or a state machine deployed on a hardware device, a computing device or any other hardware equivalents, e.g., computer readable instructions pertaining to the method discussed above can be used to configure a hardware processor to perform the steps, functions and/or operations of the above disclosed method 300 or method 400. In one embodiment, instructions and data for the present module or process 505 for determining a composition of a food (e.g., a software program comprising computer-executable instructions) can be loaded into memory 504 and executed by hardware processor element 502 to implement the steps, functions or operations as discussed above in connection with the illustrative method 300 or method 400. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method can be perceived as a programmed processor or a specialized processor. As such, the present module 505 for determining a composition of a food (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not a limitation. Thus, the breadth and scope of a preferred embodiment should not be limited by any of the above-described exemplary embodiments, but should be defined only in accordance with the following claims and their equivalents.

What is claimed is:

1. An intra-oral device comprising:
   a processor; and
   a computer-readable medium storing instructions which, when executed by the processor, cause the processor to perform operations, the operations comprising:
   detecting an act of eating via at least one sensor of the intra-oral device, wherein the at least one sensor comprises a current sensor, wherein the act of eating is detected when a current measured by the current sensor exceeds a threshold;
   activating a spectrometer of the intra-oral device to measure at least one property of at least one component in a sample of a food, in response to the detecting the act of eating via the at least one sensor, wherein the intra-oral device comprises a dental fixture, and wherein the spectrometer is embedded in the dental fixture and comprises a mass spectrometer or a spectrophotometer;
   transmitting the at least one property of the at least one component in the sample of the food to a wireless device via a wireless transmitter of the intra-oral device;
   receiving a command from the wireless device to deliver an electrical stimulation to an oral cavity in which the intra-oral device is deployed; and
   delivering the electrical stimulation in response to the command.

2. The intra-oral device of claim 1, wherein the wireless device is for:
   comparing the at least one property to a plurality of food signatures;
   determining an identity of the food based upon the comparing; and
   providing the command based upon the identity of the food that is determined.

3. The intra-oral device of claim 1, wherein the act of eating is further detected when a pH level measured by a pH sensor exceeds a second threshold.

4. The intra-oral device of claim 1, wherein the at least one sensor further comprises a moisture sensor, wherein the act of eating is further detected when a moisture level measured by the moisture sensor exceeds a second threshold.

5. The intra-oral device of claim 1, further comprising a chargeable battery, wherein the chargeable battery is for delivering electrical power to at least one of: the processor, the at least one sensor, or the spectrometer of the intra-oral device.

6. An intra-oral device comprising:
   at least one sensor for detecting an act of eating, wherein the at least one sensor comprises a current sensor;
   a spectrometer for measuring at least one property of at least one component in a sample of a food in response to the detecting the act of eating via the at least one sensor, wherein the intra-oral device comprises a dental fixture, and wherein the spectrometer is embedded in the dental fixture and comprises a mass spectrometer or a spectrophotometer;
   a wireless transceiver for transmitting the at least one property of the at least one component in the sample of the food to a wireless device and receiving a command from the wireless device to deliver an electrical stimulation to an oral cavity in which the intra-oral device is deployed; and
   electrodes for delivering the electrical stimulation in response to the command.

7. The intra-oral device of claim 6, wherein the at least one sensor further comprises a moisture sensor.

8. A method comprising:
   detecting, via at least one sensor, an act of eating, wherein the at least one sensor comprises a current sensor, wherein the act of eating is detected when a current measured by the current sensor exceeds a threshold;
   activating, via a processor, a spectrometer of an intra-oral device to measure at least one property of at least one component in a sample of a food, in response to the detecting the act of eating via the at least one sensor, wherein the intra-oral device comprises a dental fixture, and wherein the spectrometer is embedded in the dental fixture and comprises a mass spectrometer or a spectrophotometer;
   transmitting, via the processor, the at least one property of the at least one component in the sample of the food to a wireless device via a wireless transmitter of the intra-oral device;
   receiving a command from the wireless device to deliver an electrical stimulation to an oral cavity in which the intra-oral device is deployed; and
   delivering the electrical stimulation in response to the command.

9. The method of claim 8, wherein the wireless device is for:
   comparing the at least one property to a plurality of food signatures;
   determining an identity of the food based upon the comparing; and
   providing the command based upon the identity of the food that is determined.

10. The method of claim 8, wherein the detecting the act of eating further comprises detecting when a pH level measured by a pH sensor exceeds a second threshold.

11. The method of claim 8, wherein the at least one sensor further comprises a moisture sensor, and wherein the detecting the act of eating further comprises detecting when a moisture level measured by the moisture sensor exceeds a second threshold.

12. The method of claim 8, further comprising:
    delivering electrical power via a chargeable battery to at least one of: the at least one sensor, the spectrometer, the processor, or the wireless transmitter.

* * * * *